US006224585B1

(12) United States Patent
Pfeiffer

(10) Patent No.: US 6,224,585 B1
(45) Date of Patent: May 1, 2001

(54) CATHETER SYSTEM

(75) Inventor: Ulrich Pfeiffer, Munich (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/269,733

(22) PCT Filed: Aug. 7, 1998

(86) PCT No.: PCT/EP98/05033

§ 371 Date: Jul. 1, 1999

§ 102(e) Date: Jul. 1, 1999

(87) PCT Pub. No.: WO99/07429

PCT Pub. Date: Feb. 18, 1999

(30) Foreign Application Priority Data

Aug. 7, 1997 (DE) ............................................. 197 34 220

(51) Int. Cl.[7] .................................................. A61M 25/00
(52) U.S. Cl. ........................... 604/523; 600/486; 600/585
(58) Field of Search ...................... 606/42.31; 607/102; 600/549, 486, 585; 604/523, 533, 541

(56) References Cited

U.S. PATENT DOCUMENTS

| 4,718,423 | 1/1988 | Willis et al. ........................ 128/634 |
| 5,222,953 | 6/1993 | Dowlatshahi .......................... 606/15 |
| 5,279,573 | 1/1994 | Klosterman .......................... 604/171 |
| 5,443,457 | 8/1995 | Ginn et al. . |
| 5,500,012 | 3/1996 | Brucker et al. ....................... 607/122 |
| 5,514,092 | 5/1996 | Forman et al. ....................... 604/101 |
| 5,728,143 | 3/1998 | Gough et al. ......................... 607/101 |
| 5,853,409 | 12/1998 | Swanson et al. ....................... 606/31 |
| 5,921,982 | 7/1999 | Lesh et al. ............................ 606/41 |

FOREIGN PATENT DOCUMENTS

| 42 00 030 C2 | 7/1993 | (DE) . |
| 0 266 928 | 5/1988 | (EP) . |
| 0 719 519 A1 | 7/1996 | (EP) . |

OTHER PUBLICATIONS

J. Thorac Cardiovasc Surg 1987;94:286–90 *Inaccuracy of Radial Artery Pressure Measurment After Cardiac Operations*, by Rephael Mohr, M.D., Jacob Lavee, M.D., and Daniel A. Goor, M.D.

Anaesth Intens Care (1989), 17. 305–311, *A Comparison of Brachial, Femoral. and Aortic Intra–Arterial Pressures Before and After Cardiopulmonary Bypass*, by G.P. Gravlee, S.D. Bayer, M.F. O'Rourke and A.P. Avolio.

Adv. Cardiovasc. Phys., vol. 5 (Part II), pp. 16–15 (karger, Basel 1983), *A simple Device for the Continous Measurement of Cardiac Output*, by K.H. Wesseling, B.de Sit, J.A.P. Weber, N. Ty Smith.

*A Fiberoptics–Based System for Integrated Monitoring of Cardiac Output. Intrathoracic Blood Volume. Extravasccular Lung Water. $O_2$Saturation and a–v Differences*, by U.J. Pfeiffer, G. Backus, G. Blumel, J. eckert, P. Muller, P. Winker, J. Zeravik, and G.H. Zimmerman.

Primary Examiner—Wynn Wood Coggins
Assistant Examiner—Kevin C. Sirmons
(74) Attorney, Agent, or Firm—Nixon Peabody LLP; Donald R. Studebaker

(57) ABSTRACT

A catheter system comprising a catheter including a tip having a distal opening, a first opening, and a guide wire lumen extending from the distal opening to the first opening provided on a surface of the catheter, and a guide wire having a length substantially smaller than a length dimension of the catheter. The catheter system in accordance with the present invention may include a sensor lumen and a pressure lumen. The sensor lumen terminates at the first opening and includes an optically transparent closure and the pressure lumen includes a second opening. In the preferred embodiment, the first opening and the second opening are positioned on the catheter at substantially same axial distance from the distal opening and further includes a perforation that allows fluidic communication between the pressure lumen and the first opening. The catheter system may also comprise a pressure hose, at least one optical fiber and a thermal sensor element. Furthermore, the catheter system may further comprise a three-way valve, a pressure transducer, a flushing valve, a flow controller, and a drip chamber.

9 Claims, 3 Drawing Sheets

CATHETER SYSTEM

BACKGROUND OF THE INVENTION

1. Field of the Invention

This invention relates to a catheter systems with a guide wire and a catheter. More specifically, this invention relates to such catheter systems in which at a distal end of the catheter at a tip, there is provided a guide wire lumen which extends from the tip to an opening provided laterally in the catheter.

2. Description of the Prior Art

Placement of catheters through small blood vessels is currently done essentially by means of a technology combining two different processes. In the standard process, the radial artery is used to monitor the arterial blood pressure and the arterial blood gases, especially in the perioperative area under anesthesia. Generally, in this standard process, a single-lumen intravasal catheter of teflon or of polyurethane with a length between 3 cm and 5 cm and with a diameter up to 18 gauge are inserted into the radial artery. Catheters are inserted conventionally via a guide cannula which fills the lumen of the catheter and projects above it. In addition, the arterial pressure is generally measured invasively by means of a liquid coupling to an external pressure transducer. Blood gases and other physiological parameters are determined from blood samples which are collected through the catheter lumen.

One disadvantage of the existing technique of puncturing the radial artery and inserting the above described catheter into the vascular lumen is that the catheter cause a reactive constriction of the radial artery and thus, interruption of the blood flow on the catheter often occurs. This, in turn, results in incorrect pressure measurements which is described by R. Mohr, J. Lavee and D. A. Goor in "*Inaccuracy Of Radial Artery Pressure Measurement After Cardiac Operations*" published in the J. Thorac. Cardiovascular Surg. 94(2), 286–290 (1987). This pressure measurement is erroneously interpreted as being accurate while in fact, the pressure measurement is inaccurate because it is acquired by measuring a pulsating stagnating blood column.

If blood is taken via the pressure/blood collection lumen of the catheter, the biochemical or physiological values of the sample often do not agree with the actual values since this blood originates, at least in part, from a blood column which is not being circulated. Analogous inaccurate measurements arise when a relatively short radial catheter is provided with sensors for measuring biochemical or physiological parameters such as blood gases.

In addition, central arterial pressure curves is necessary in critical situations. However, pressure curves in the radial artery generally deviate dramatically from pressure curves measured in central arteries such as the aorta, both in the shape of the pressure curve, and in systolic and diastolic blood pressures. This deviation is discussed by G. P. Gravlee, S. D. Brauer, M. F. O'Rourke, and A. P. Avolio in "*A Comparison Of Brachial, Femoral And Aortic Intra-Arterial Pressures Before And After Cardiopulmonary Bypass*" published in Anaesth. Intensive Care, 17(3), 305–311 (1989).

Peripheral-arterial pressure curves from the radial artery are also not suitable for computing the cardiac output using the pulse contour method because an unambiguous diagnosis of the ejection phase of the left ventricle is not possible. Centrally measured pressure curves are required for this purpose. This is discussed by K. H. Wesseling, B. de Wit, A. P. Weber, N. Ty Smith in "*A Simple Device For The Continuous Measurement Of Cardiac Output*" published in Adv. Cardiovasc. Phys., vol 5 (Part II); 16–52 (1983).

The cardiac output and circulatory filling state in the perioperative area are generally determined through a pulmonary-arterial thermodilution catheter placed within the radial artery in addition to the arterial radial catheter. In the surgical arts, the pulmonary-arterial thermodilution catheter is also known as a pulmonary catheter or a pulmonary arterial catheter. In pulmonary arterial thermodilution, a glucose or saline solution which has a temperature which deviates from the blood temperature is venously injected. The pulmonary arterial catheter placed in the pulmonary artery includes a temperature sensor on the distal end which allows recording of the thermodilution curve. For example, the cardiac output is computed from the thermodilution curve by means of the Stewart-Hamilton process. Furthermore, by inflating a balloon placed on the distal end of the catheter, a pulmonary arterial closing pressure is recorded which will provide information on the circulatory fill status.

The cardiac output and the circulatory fill status can also be measured by means of transcardiopulmonary arterially measured thermodilution as discussed in U.S. Pat. No. 5,526,817 to U. J. Pfeiffer and R. Knoll or also by means of thermo-dye dilution as discussed by U. J. Pfeiffer, G. Backus, G. Bluemel, J. Eckart, P. Mueller, P. Winkler, J. Zeravik, and G. J. Zimmerman in "*A Fiberoptics-Based System For Integrated Monitoring Of Cardiac Output, Intrathoracic Blood Volume, ExtravascularLung Water, $O_2$ Saturation, And a-v Differences, Practical Applications OfFiberoptics In Critical Care Monitoring*" published in Springer Verlag, p. 114–125 (1990). However, existing measurement catheters allow simple and reliable measurements in the femoral artery and in the abdominal aorta.

Experience shows that the currently available arterial thermodilution and thermo-dye dilution catheters with a blood pressure lumen having an extremely small diameter of 1.33 mm still do not allow reliable thermo- or thermo-dye dilution measurements in the radial artery because they can only be placed into position by an insertion catheter with a much larger outside diameter. However, measurement through the radial artery is necessary during anesthesia because during many surgeries, the anesthetist does not have any opportunity to correct the location of the femoral catheter. In addition, such measurements may also be required if as a result of the completed surgery, there is no blood flow in the femoral artery or the blood flow it is influenced by the surgeon.

The disadvantages of the existing arterial thermo- or oximetry/thermo-dye dilution catheters include the fact that the sensors such as a fiber optic eye or a thermistor have been attached to the distal end and end flat on the catheter end next to the opening of the blood pressure lumen. In addition to the insertion of the measurement catheter, this requires the use of an additional insertion catheter which pushes the measurement catheter into the blood vessel. Consequently this system results in a much larger puncture surface and thus, can cause damage to the blood vessel wall and reduce blood flow because of the greater diameter.

Furthermore, the fiber optic eye which is often unprotected on the tip of the catheter, is frequently blinded since the catheter tips adjoin certain structures of the vessel wall such as branches, atherosclerotic changes, etc. and its function can be adversely effected because of formation of a microthrombus.

The German reference DE 42 00 032 C2 discloses a catheter system of the type to which the present invention is directed. This known catheter is preferably provided with a dilation balloon, by means of which constricted vessels, for example coronary vessels, can be widened. A catheter of this type is usually inserted via a lock attached to the femoral artery of the patient, and is pushed into the coronary system via the patient's aorta as disclosed in the German reference DE 42 00 030 C2. In this manner, the catheter is guided by the guide wire in the area of the catheter tip whereas in the proximal catheter area adjacent to the catheter tip, it is guided by the parallel guide wire lying outside the catheter but within the blood vessel.

The guide wire is thus used in the catheter system known from DE 42 00 030 C2, to guide the catheter tip within the blood vessel system. Due to the necessity of using an insertion catheter or a lock, the insertion of this catheter requires a comparatively large puncture surface. Due to the long length of the guide wire (which usually has at least the length of the catheter, but generally have twice the length of the catheter), a large sterile surgical field is necessary since the guide wire can easily come into contact with articles in the vicinity of the patient during its insertion.

The published European Patent Application EP 0 266 928 A1 discloses a multifunction cardiovascular catheter system but fails to disclose the use of a guide wire.

SUMMARY OF THE INVENTION

In view of the foregoing, it is an object of the present invention to provide a catheter system that can be quickly and easily placed in small blood vessels, for example in the radial artery, by means of direct guide wire technique with little traumatizing effect.

A second object of the present invention is to provide a catheter system which can ensure that the sensor or the sensors on or in the catheter comes to rest in an area of the vessels in which blood flows past the catheter and in an area in which the shape of the blood pressure curve closely corresponds to that in the aorta when placed in the arterial system.

Another object of the present invention is to provide a catheter system with a relatively short guide wire in order to make the sterile covering as small as possible when the blood vessel is punctured.

Yet, still another object of the present invention is to provide a catheter system wherein the catheter remains positionable and repositionable under sterile conditions.

These objects are achieved by providing a catheter system comprising a catheter including a tip having a distal opening, a first opening, and a guide wire lumen extending from the distal opening to the first opening provided on a surface of the catheter, and a guide wire having a length substantially smaller than a length dimension of the catheter. In one embodiment, the guide wire is substantially 20 cm in length and the length dimension of the catheter is substantially 50 cm. The catheter system in accordance with the present invention may include a sensor lumen and a pressure lumen. The sensor lumen terminates at the first opening and includes an optically transparent closure and the pressure lumen includes a second opening. In the preferred embodiment, the first opening and the second opening are positioned on the catheter at substantially same axial distance from the distal opening and further includes a perforation that allows fluidic communication between the pressure lumen and the first opening.

In another embodiment of the present invention, these objects are achieved by providing a catheter system further comprising a pressure hose, at least one optical fiber and a thermal sensor element. The pressure hose is connected to a proximal end pressure opening of the pressure lumen. The optical fiber is positioned within the sensor lumen and terminates at the optically transparent closure and emerges at a proximal end sensor opening of the sensor lumen. The thermal sensor element is positioned within the sensor lumen and includes a signal connection which emerges from the proximal end sensor opening of the sensor lumen. In addition, a three-way valve connected to said pressure hose by a lateral Luer lock connection may also be provided. The pressure hose can be in fluidic communication with a pressure transducer that includes a connecting plug to allow electrical communication with a pressure monitor. The pressure hose can also be connected to a flushing valve which is in fluid communication with a flow controller, which in turn, may also be in fluid communication with a drip chamber.

With the catheter system in accordance with the present invention, it becomes possible to push the catheter into the vicinity of the aorta, for example via a minimally traumatizing puncture of the radial artery, in order to take measurements, like blood pressure measurements or optical spectral measurements, which are far superior than previous measurements possible through a puncture of the radial artery.

The improved catheter system in accordance with the present invention is used in the manner described below. The radial artery is punctured in the conventional manner by means of a cannula. Then, the short guide wire is pushed via the lumen of the cannula into the blood vessel and the cannula is withdrawn while holding the guide wire stationary. The puncture side of the blood vessel is widened by a dilator. Then, the dilator is likewise withdrawn, leaving the guide wire in the vessel. The guide wire is then threaded into the distal opening in the tip and the catheter is pushed forward. The guide wire is pushed forward far enough to allow the guide wire to project out of the first opening on a surface of the catheter so that it can be securely gripped by the surgeon with his or her fingers. Then, by using the guide wire, the catheter is pushed roughly 5 cm through the skin and the subcutaneous tissue into the blood vessel. Before the first opening of the guide wire lumen enters the blood vessel, the guide wire is pulled. Subsequently, the catheter (without the guide wire) is pushed forward approximately another 50 cm so that its tip reaches a large artery (for example, the axillary artery). The attachment of the catheter is minimally traumatizing since only the easily accessible radial artery need be punctured and the use of a lock is not necessary. Because the guide wire is short, the sterile field can be kept very small without the danger of contamination of the guide wire during the insertion.

In contrast to the teachings of the prior art German reference DE 42 00 030 C2, the short guide wire provided in the present invention is not used to guide the catheter within the blood vessel system, but rather to insert the catheter through the puncture site into the blood vessel system. Therefore, in contrast to the German reference DE 42 00 030 C2, the short guide wire provided in the present invention replaces the lock or insertion cannula usually necessary for insertion of catheters. Thus, the present catheter system is substantially different than that disclosed in the German reference DE 42 00 030 C2 and fulfills a completely different purpose. More specifically, the guide wire as disclosed in DE 42 00 030 C2 has a length which is at least equal to the length of the catheter since it is used to insert the catheter along with the guide wire into small blood vessels, for example into the coronary system.

These and other objects, features and advantages of the present invention will become more apparent from the following detailed description of the preferred embodiments of the intention when viewed in conjunction with the accompanying drawings.

DETAILED DESCRIPTION OF THE INVENTION

Figure 1:
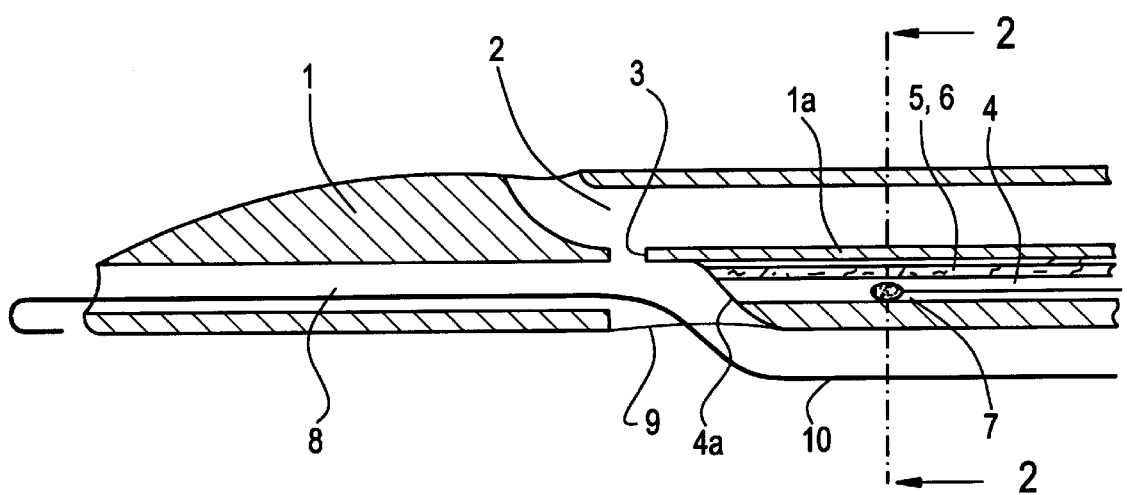
FIG. 1 shows an enlarged longitudinal cutaway view of a catheter system in accordance with one embodiment of the present invention.

In the following, various embodiments of a catheter system in accordance with the present invention are specifically described and illustrated which will attain the advantages noted previously. In this regard, the same or similar parts are indicated with the same reference numerals in the illustrated FIGS. 1 to 4. The catheter system illustrated in FIGS. 1 to 4 are shown as an example of the claimed invention and has a useful intravasal length of roughly 50 cm and a diameter of roughly 1.3 mm to allow it to be used in adults of normal weight and size. Of course, these dimensions are provided as an example only and other dimensions may be used in accordance with the present invention according to the specific needs and the specific application.

Figure 2:
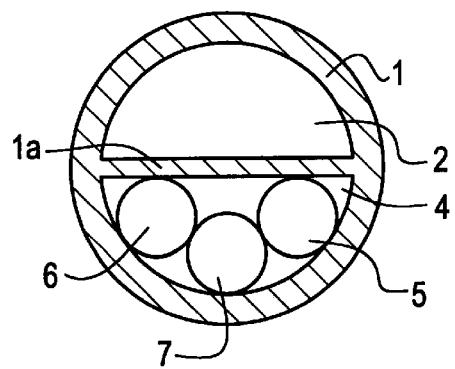
FIG. 2 shows a transverse cutaway of the catheter system of FIG. 1 as viewed along the dashed line II—II.

As shown in FIG. 1 and more clearly in FIG. 2, the catheter 1 in this embodiment includes a shaft wall 1a thereby creating two lumens within the catheter 1. The catheter 1 and the shaft wall 1a may be integrally formed from a slightly thrombogenic material such as polyurethane. Of course, the specific geometry of the shaft wall 1a and the material is provided as an example only and other shapes and materials may also be used in accordance with the present invention. As can be clearly seen in FIG. 2, the two lumens created by the shaft wall 1a each serve differing functions as will be described hereinbelow. The first lumen is a sensor lumen 4 in which sensor lines, such as fiber optic and/or thermistor connecting lines, are guided. The other lumen is a pressure lumen 2 which is used to collect blood and measure pressure over a liquid column. In addition, in an alternative embodiment, the catheter 1 can also be provided with length marks (not shown) and an x-ray contrast strip (not shown).

At a distal end near a conically shaped tip 1b, the catheter 1 includes a molded guide wire lumen 8 by which a guide wire 10 can be pushed. The guide wire lumen 8 is substantially shorter than the length of the catheter 1. In this example, the guide wire lumen may be roughly 20 cm where the catheter 1 may be 50 cm. The guide wire lumen 8 extends roughly 5 cm from the tip 1b of the catheter 1 and includes a distal opening 1c and a first opening 9a such that a portion of the guide wire 10 is within the guide wire lumen 8 while the remainder of the guide wire 10 is outside the catheter 1.

The sensors used in the catheter system in accordance with the present embodiment are position within the sensor lumen 4. These sensors which may include an optically transparent closure 4a, such as a fiber optic eye, and thermistors 5 and 6 (shown in FIG. 2), are attached proximally bordering the first opening 9a which is relatively large. The flat surface of the optically transparent closure 4a, such as a fiber optic eye, is located at an angle of less than 90 degrees to the longitudinal dimension of the catheter 1, and the optically transparent closure 4a ensures a way to access light emission and light reflection into or out of the blood flowing past the catheter 1. A heparinized flushing solution may be provided continually to the optically transparent closure 4a, such as a fiber optic eye, by way of a perforation 3 in the shaft wall 1a in order to prevent formation of islands of coagulation on the optically transparent closure 4a. On the contralateral side of the catheter 1 which forms the pressure lumen 2, a second opening 9b is provided behind the tip 1b through which the pressure and blood collecting lumen 2 can also be continually flushed by heparinized flushing solution. In the present embodiment, the second opening may be roughly 3 cm. Furthermore, a thermal sensor element 7 may also be provided in the sensor lumen 4 to provide accurate measurement of temperature.

Figure 3:
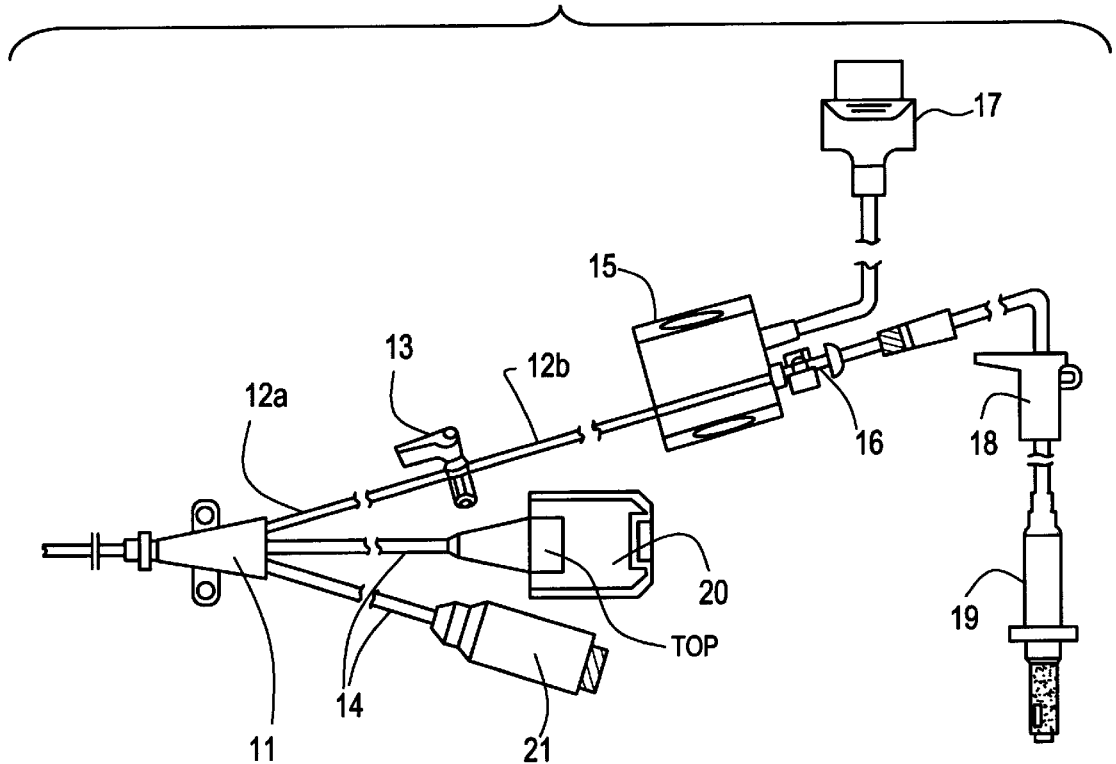
FIG. 3 shows a panoramic view of the catheter system of FIG. 1 with various components divided along various portions of the canal for clarification.

FIG. 3 illustrates one embodiment of the catheter system in accordance with the present invention. As can be seen, the various components have been illustrated separately with the interconnections between each component being shown discontinuous for the sole purpose of indicating that the length of the interconnections between the components can vary depending on the particular embodiment and the particular application. As also clearly shown in FIG. 3, a canal division 11 is provided on the proximal end of the intravasal portion of the catheter 1. The canal division 11 may include long canal extensions 12 of roughly 10 cm for communication with various components of the catheter system. Of course, each of the canal extensions 12 may be tailored for communication with a particular component. For example, the canal extension 12a may be in communication with a pressure hose 12b while the remaining canal extensions 12 may be in communication with signal lines 14 provided for signal communication with various sensor connectors such as a fiber optic plug 20 and a thermistor plug 21.

As also illustrated, a three-way valve 13 may be provided through a lateral Luer lock connection between the canal extension 12a and the pressure hose 12b. An additional pressure hose (not shown) may also be provided in connection with the three-way valve 13 for easier zero point adjustment of a pressure transducer system which will be discussed hereinbelow. The pressure hose 12b is in turn, in communication with an electronic pressure transducer 15 having low compliance to allow accurate measurement of pressure within the pressure hose 12b. Air accumulation on the otherwise conventional connectors is clearly reduced by using solid flange connections. Furthermore, the entire inner surface of the pressure lumen 2, the canal extension 12a, and the pressure hose 12b may be made as smooth as possible to ensure that the pressure transducer 15 senses accurate pressures from the catheter 1 with minimal fluidic pressure loss.

Figure 4:
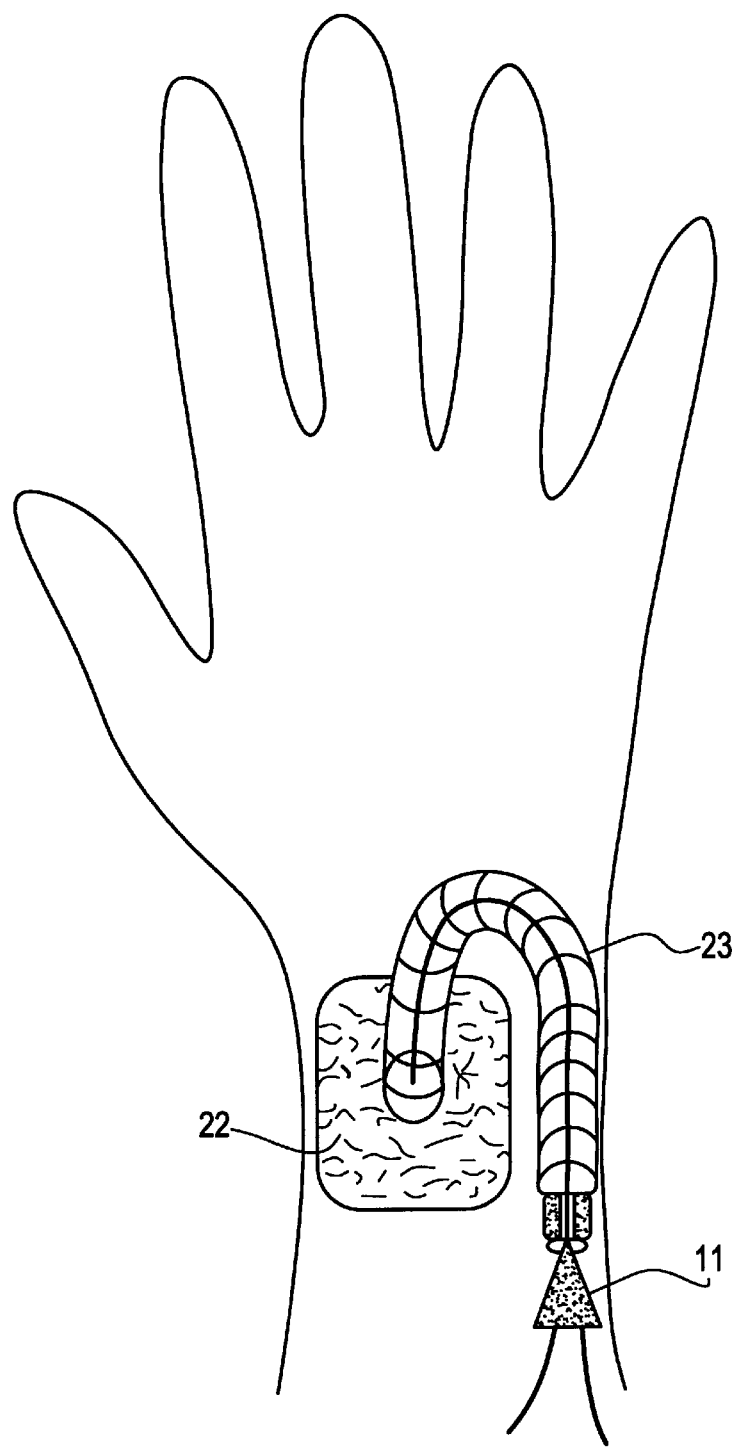
FIG. 4 shows the canal division of the catheter system from FIG. 1 in use.

As is apparent from FIG. 4, an adhesive film 22 is attached directly to the canal division 11 of the catheter 1. The adhesive film 22 is sterile and may be transparent and highly adhesive and may also be provided with an integrated protective hose 23 which may be roughly 10 cm long. In this manner, by providing the sterile, adhesive film 22 and an integrated protective hose 23, optimum initial positioning and repositioning of the catheter 1 is enabled such as when the sensor is mispositioned.

It should be noted that the short guide wire 10, which may be roughly 20 cm long, is an important component of the catheter system in accordance with the present invention. This guide wire 10 has a diameter to fit within the relatively short guide wire lumen 8 of the catheter 1. A cannula (not shown) with an inside diameter adapted to the guide wire 10 and a dilator of roughly 5 cm long and roughly 1.3 mm in diameter can also be added thereto.

The use of the catheter system as claimed in the present invention as illustrated in FIGS. 1 to 4 is discussed hereinbelow. Initially, in accordance with one embodiment of the present invention, the various components for collecting blood and measuring its pressure, including the communicating components such as the canal extension 12a and the pressure hose 12b, are filled with a liquid such as a heparinized physiological saline solution through a flushing valve 16, a flow regulator 18 and a drip chamber 19. The pressure transducer 15 is electrically connected to a pressure monitor (not shown) by means of a connecting plug 17.

By means of a cannula (not shown), the radial artery is punctured in the conventional manner. Then the short guide wire 10 is pushed through the lumen of the cannula into a blood vessel (not shown) and the cannula is withdrawn from the blood vessel while holding the guide wire 10 stationary within the vessel. The punctured side of the blood vessel is widened by means of a dilator (not shown) via the guide wire 10. The dilator is likewise withdrawn, leaving the guide wire 10 within the vessel. Then the guide wire 10 is threaded into the distal opening 1c in the tip 1b of the catheter 1 and is pushed forward through the short guide wire lumen 8 such that the guide wire 10 emerges through the first opening 9a and extends far enough away from the guide wire lumen 8 such that it can be securely gripped by the surgeon using his or her fingers.

Then the catheter 1 is pushed roughly 5 cm through the skin and subcutaneous tissue (not shown) into the blood vessel (not shown) using the guide wire 10. The guide wire 10 is then pulled. Afterwards the catheter 1 is pushed forward another roughly 50 cm until its tip 1b comes to rest in a large artery such as an axillary artery. The proper positioning of the tip 1b can be recognized by monitoring the shape of the blood pressure curve recorded simultaneously through the pressure lumen 2.

For zero point adjustment, the three-way valve 13 can be opened to the atmosphere and moved to the height of the heart by lifting the patient's arm. If such a zero point adjustment is not possible by lifting the arm, it may also be attained by connecting a pressure hose at least 50 cm long to the Luer lock connection of the three-way valve 13 and creating a liquid column which is open to the atmosphere and which corresponds to the height of the heart.

The catheter system in accordance with the present invention ensures reliable acquisition of physiological or biochemical parameters through placement of the various sensors in the flow area near the aorta when the catheter 1 is inserted through a small artery such as the radial artery. The above described embodiment of the catheter system in accordance with the present invention enables pressure to be measured near the aorta. Correspondingly, this also provides a reliable evaluation of the pressure signal using the pulse contour method, reliable acquisition of transcardiopulmonary indicator dilution curves and continuous oxygen saturation measurements. Of course, the present invention may be easily modified and extended to measure other parameters of interest depending on the circumstances and application.

The catheter 1 can be inserted into peripheral arteries which are located near the surface by means of a short guide wire 10 and through a guide wire lumen 8. This reliable and simple method eliminates the need for using a catheter insertion system currently known in the art which only yields inaccurate results in many applications. With the same measurement catheter diameter, it now becomes possible to insert the catheter 1 into smaller arteries such as the radial artery. By means of this new technique using the short guide wire 10, the sterile area which must be formed for insertion can be made much smaller than would be necessary when using conventional prior art insertion sets with long guide wires.

The arrangement of the sensors which is set back from the catheter tip 1b ensures that they can always be optimally placed in flowing blood and their function is not disrupted by certain vascular structures. Furthermore, direct flushing of the optically transparent closure 4a can be done via the perforation 3 in the shaft wall 1a.

By providing direct communication between the pressure transducer 15 and the catheter 1, optimum pressure measurements can be obtained through a relatively thin pressure lumen 2 since the accumulation of air bubbles which attenuate the pressure signal is prevented by the smooth inner surfaces of the pressure lumen 2, the canal extension 12a, and the pressure hose 12b that extend to pressure transducer 15.

Experience with many sensor systems, such as fiber optic system, shows that for ideal measurement processes, correction of the catheter position may be necessary from time to time. Through practicing the present invention, this correction of the catheter position and the optimum initial positioning of the catheter system are ensured by the integrated protective hose 23 and the adhesive film 22.

From the foregoing, it should now be apparent how the present invention provides an improved catheter system that can be quickly and easily placed in small blood vessels by means of direct guide wire technique with little traumatizing effect. It should also be apparent how the present invention provides a catheter system that ensures that the sensors comes to rest in an area of the vessels in which the shape of the blood pressure curve closely corresponds to that in the aorta. In addition, it should also be apparent how the present invention provides a catheter system with relatively short guide wire in order to make the sterile covering as small as possible and allows the catheter to be repositionable under sterile conditions.

Furthermore, it can be seen how the above catheter system in accordance with the present invention avoids the disadvantages of the prior art systems by providing a short guide wire to insert the catheter through the puncture site into the blood vessel system. Thus, the short guide wire provided in the present invention replaces the lock or insertion cannula usually necessary for insertion of catheters.

While various embodiments in accordance with the present invention have been shown and described, it is understood that the invention is not limited thereto, and may be changed, modified and further applied by those skilled in the art. Therefore, this invention is not limited to the details shown and described previously, but also includes all such changes and modifications which are encompassed by the appended claims.

What is claimed is:

1. A catheter system comprising:
 a catheter including a tip having a distal opening, a first opening, and a guide wire lumen extending from said distal opening to said first opening, said first opening provided on a surface of said catheter;

a guide wire having a length substantially less than a length dimension of said catheter;

a pressure lumen extending in a longitudinal direction of said catheter;

a sensor lumen extending in a longitudinal direction of said catheter;

a pressure hose connected to a proximal end of a pressure opening of said pressure lumen, a pressure transducer in fluidic communications with said pressure hose; said pressure transducer including a connecting plug to allow electrical communication with a pressure monitor; and a flushing valve connected to said pressure hose and in fluid communication with a flow controller which is in fluid communication with a drip chamber.

2. Catheter system of claim 1, wherein said length dimension of said catheter is at least 10 cm.

3. Catheter system of claim 2, wherein said guide wire is substantially 20 cm in length and said length dimension of said catheter is substantially 50 cm.

4. Catheter system of claim 1, wherein said sensor lumen terminates at said first opening and includes an optically transparent closure.

5. Catheter system of claim 1, wherein said pressure lumen includes a second opening.

6. Catheter system of claim 5, wherein said first opening and said second openings are positioned on said catheter at a substantially same longitudinal distance from said distal opening.

7. Catheter system of claim 5, wherein said catheter further includes a perforation for allowing fluidic communication between said pressure lumen and said first opening.

8. Catheter system of claim 7 further comprising:

at least one optical fiber positioned within said sensor lumen, said optical fiber terminating at said optically transparent closure and emerging at a proximal end sensor opening of said sensor lumen; and a thermal sensor element positioned within said sensor lumen, said thermal sensor element including a signal connection which emerges from said proximal end sensor opening of said sensor lumen.

9. Catheter system of claim 8, further comprising a three-way valve connected to said pressure hose by a lateral Luer lock connection.

* * * * *